United States Patent [19]

Anderson et al.

[11] 4,352,929
[45] Oct. 5, 1982

[54] 1,3-THIAZIN-4-ONE

[75] Inventors: David J. Anderson, Kalamazoo; Barbara E. Loughman, Richland, both of Mich.

[73] Assignee: The Upjohn Company, Kalamazoo, Mich.

[21] Appl. No.: 268,467

[22] Filed: May 29, 1981

Related U.S. Application Data

[62] Division of Ser. No. 64,783, Aug. 8, 1979.

[51] Int. Cl.$^3$ .................................. C07D 279/06
[52] U.S. Cl. ................................ 544/54; 424/246
[58] Field of Search ............................... 544/54

[56] References Cited

U.S. PATENT DOCUMENTS

| | | | |
|---|---|---|---|
| 2,585,064 | 2/1952 | Wheeler et al. | 544/54 |
| 3,149,106 | 9/1964 | Loev | 544/54 |
| 3,732,216 | 5/1973 | Weinstock | 544/54 |
| 3,781,434 | 12/1973 | Berkoff et al. | 424/246 |
| 3,816,627 | 6/1974 | Weinstock | 424/246 |
| 4,169,899 | 10/1979 | Shiroki et al. | 544/54 |

OTHER PUBLICATIONS

Garraway, *Chemical Soc., Jour.*, London (1961), pp. 3733–3735.

*Primary Examiner*—John M. Ford
*Attorney, Agent, or Firm*—Joan Thierstein; Sidney B. Williams, Jr.

[57] ABSTRACT

Novel cyclized ω-carboxyethyl mono- or dithiocarbanilic acids are disclosed as immunoregulatory agents, useful in the treatment of organ transplant reject phenomenon and autoimmune diseases particularly where a delayed hypersensitivity component has been established, such as multiple sclerosis.

Additionally described is the use of certain cyclized ω-carboxyalkyl mono- or dithiocarbamic acids and certain cyclized ω-carboxyalkyl mono- or dithiocarbamic acids.

10 Claims, No Drawings

1,3-THIAZIN-4-ONE

This is a division of application Ser. No. 064,783, filed Aug. 8, 1979.

BACKGROUND OF THE INVENTION

1. Field of the Invention

The present invention provides certain novel organic compounds which have immunoregulatory properties, rendering these compounds useful in the treatment of hyperimmunity diseases. Moreover, the present invention provides for the immunoregulatory use of certain organic compounds in hyperimmunity diseases.

Among the novel compounds herein and the compounds employed in the novel methods herein as pharmacological agents are cyclized substituted ω-carboxymethyl and ω-carboxyethyl mono- or dithiocarbanilic acids and cyclized substituted ω-carboxymethyl and ω-carboxyethyl mono- or dithiocarbamic acids.

Cyclized ω-carboxymethyl and ω-carboxyethyl mono- or dithiocarbanilic acids have the structural formula:

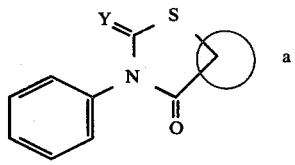

wherein
Y is selected from the group consisting of oxygen and sulfur;
a is the integer one or two; and corresponding cyclized ω-carboxymethyl and ω-carboxyethyl mono- or dithiocarbamic acids are compounds of the structural formula:

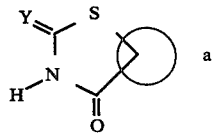

wherein Y and a are as defined above.

Compounds of the above structures are known as thiazines and thiazolines which may be rhodanines.

2. The Prior Art

Certain thiazines and rhodanines are known in the art as useful for a wide variety of purposes. Compounds within these classes are structurally derived from corresponding intermediates which are prepared, for example, by reactions between ω-mercaptoalkylcarboxy acids and isocyanates or isothiocyanates. Subsequent dehydration results in internal cyclization of the intermediates with yields of thiazines and rhodanines. Dehydration is accomplished with addition of acetic anhydride containing a few drops of strong acid. Methods to prepare certain intermediates and the cyclized derivatives of the present invention are well known.

See, for example, Garroway, J. L., J. Chem. Soc. 1961:3733–5 which describes ω-carboxyalkyl dithiocarbanilic acids as precursors for corresponding cyclic lactams, i.e. rhodanines and thiazine analogs. For production of rhodanine or thiazine analogs from corresponding ω-carboxyalkyl dithiocarbanilic acid precursors see also U.S. Pat. Nos. 3,781,434; 3,732,216 and 3,816,627; Brown, F. C., et al., J.A.C.S. 78:384 (1956); Werbel, L. M., et al., J. Med. Chem. 11 (2):364 (1968) and a Belgian application 862,725, filed July 13, 1978 having Derwent Number 33497A/19 by Yoshitomo Pharm. Ind. KK (also now issued as U.S. Pat. No. 4,169,899).

The United States patents noted above describe the antiarthritic use of two groups of substituted thiazines, including, inter alia, compounds of the formula:

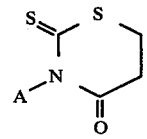

wherein according to U.S. Pat. Nos. 3,781,434 and 3,732,216 "A" represents phenyl substituted by a halogen such as chlorine, bromine and fluorine or trifluoromethyl and wherein according to U.S. Pat. No. 3,816,627 "A" represents a heterocyclic moiety, particularly one containing nitrogen. In the Yoshitomo Belgian Application "A" includes an alkylene linkage having one to five carbons between the nitrogen on the thiazine and any other moiety thereon which therefore distinguishes it from the present invention.

The remaining references listed above describe certain rhodanines as anti-fungicidal, anti-bacterial and anti-malarial agents.

W. Hanefeld, Archio Der Pharmazie Vol. 308, (1975) pp, 450–454 describes fungiostatic properties of certain dioxo and thioxo tetrahydro-1,3-thiazines.

Immunoregulatory agents may be either immunosuppressive or immunostimulatory. For the purposes of this invention, the process of immunosuppression is the desired response to a disease or other condition which results from hyperimmunity in the animal or patient. Immunosuppressive use of ω-carboxyalkyl and ω-(alkoxycarbonyl)alkyl esters of dithiocarbanilic acid and certain arylsubstituted acids related thereto are found in U.S. Pat. No. 4,110,444 and copending Ser. No. 848,433, now abandoned. For a comprehensive review of the use of immunosuppressive agents in the treatment of hyperimmunity diseases, see Camiener, G. W., et al., Progress in Drug Research 16:67 (1972) and Wechter, W. J., et al., Progress in Drug Research 20:573 (1976).

Many known immunosuppressive agents are cytotoxic and are believed in part, if not exclusively, to accomplish the immunosuppressive effects via a cytotoxic mechanism on the immunoactive organs (e.g. bone marrow and thymus) and on the proliferating dynamic primary and secondary lymphold tissue. For example, known antineoplastic agents such as cyclophosphamide, have been used in the treatment of arthritis. See Skinner, M. D., et al., Rheumatology 5:1 (1974).

Finally, anthelmintics such as niridazole have been employed immunosuppressively to control allograft rejection; while another anthelmintic, levamisole, is apparently a non-specific stimulator of the immune system. See Daniels, J. D., et al., J. Immuno 115:1414 (1975) and Renorex, G., et al., J. Immun. 109:761 (1972).

SUMMARY OF THE INVENTION

The present invention provides novel organic compounds selected from the group consisting of:

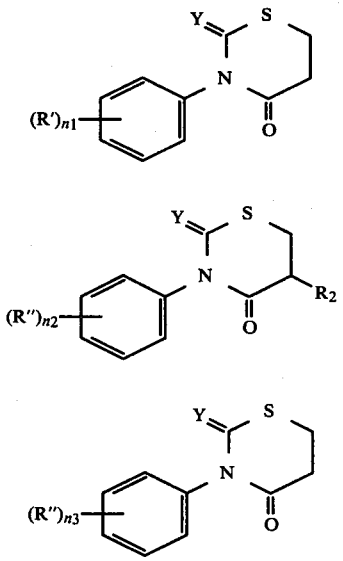

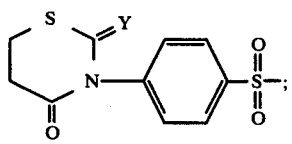

wherein
R' is alkyl carbonyl with alkyl of from one to four carbon atoms, inclusive; or

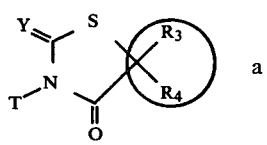

R'' is selected from the group consisting of chloro, bromo, fluoro and trifluoromethyl; and
$R_2$ is selected from the group consisting of hydrogen and acylamino with acyl of from one to four carbon atoms, inclusive;
$n_1$ is an integer of from one to three;
$n_2$ is an integer of from one to five;
$n_3$ is an integer of from three to five;
Y is selected from the group consisting of oxygen and sulfur.

The invention also relates to a method of producing immunosuppression in a mammal exhibiting a hyperimmunity disease which comprises systemically administering in a pharmaceutically acceptable dosage a compound selected from the group consisting of:

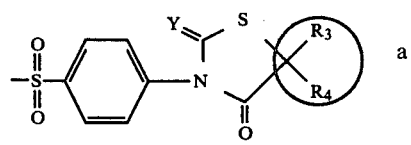

T is selected from the group consisting of hydrogen, lower alkyl of from one to four carbon atoms, inclusive, amino, carboxybenzylideneamino, chlorobenzylideneamino, anilino, phenylalkyl with alkyl of from one to four carbon atoms, inclusive, cycloalkyl, and

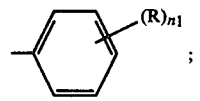

wherein
R is selected from the group consisting of hydrogen, alkyl of from one to four carbon atoms, inclusive, alkoxy of from one to four carbon atoms, inclusive, thioalkoxy of from one to four carbon atoms, inclusive, alkylcarbonyl with alkyl of from one to four carbon atoms, inclusive, acyloxy with acyl of from one to four carbon atoms, inclusive, nitro, acylamino; and

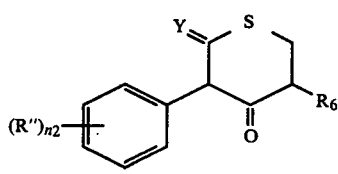

$R_3$ and $R_4$ are the same or different and are selected from the group consisting of hydrogen, alkyl of from one to four carbon atoms, inclusive, —CH$_2$CO$_2$H and pharmaceutically acceptable salts thereof, alkoxymethyl with alkoxy of from one to four carbon atoms, inclusive, and indanylmethylene; such that when $R_3$ and $R_4$ are different one of the selection is hydrogen;
Y is selected from the group consisting of oxygen and sulfur;
$n_1$ is an integer of from one to three; and
a is the integer one or two;

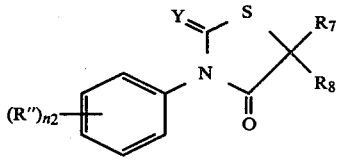

wherein
$R_6$ is selected from the group consisting of hydrogen and acylamino of from one to four carbon atoms, inclusive;
R'' is selected from the group consisting of chloro, bromo, fluoro and trifluoromethyl;
Y is defined as above;
$n_2$ is an integer of from one to five;

wherein
$R_7$ and $R_8$ are the same or different and are selected from the group consisting of hydrogen, alkyl of from one to four carbon atoms, inclusive, carboxyalkyl and pharmaceutically acceptable salts thereof; such that when $R_7$ and $R_8$ are different one of the selection is hydrogen;

R" is selected from the group consisting essentially of bromo, chloro, fluoro and trifluoromethyl;
Y is defined as above; and
$n_2$ is an integer of from one to five; and

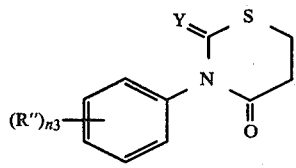 (d')

R" is selected from the group consisting of fluoro, chloro, bromo and trifluoromethyl;
$n_3$ is an integer of from three to five, and
Y is as defined above;
wherein compounds (a'), (b'), (c') and (d') are all administered in an amount effective to ameliorate or cure said hyperimmunity disease.

The invention further relates to a method of immunosuppression in a mammal exhibiting a hyperimmunity disease of the class comprising transplant rejection phenomena and autoimmune diseases such as psoriatic arthritis, systemic lupus erythemotosus, regional enteritis, chronic active hepatitis, nephrotic syndrome, glomerulonephritis, lupus nephritis, ulcerative colitis and particularly where a delayed hypersensitivity component has been established such as multiple sclerosis, which comprises systemically administering in a pharmaceutically acceptable dosage a compound of the formula:

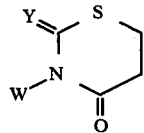

wherein W is pyridyl or

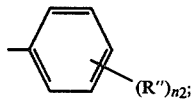

wherein
R" is selected from the group consisting of chlorine, bromine, fluorine, and trifluoromethyl;
$n_2$ is an integer of from one to five; and
Y is as defined above;
in an amount effective to ameliorate or cure said hyperimmunity disease.

A preferred embodiment of the invention is a method of producing selective immunosuppression in a mammal exhibiting a hyperimmunity disease which comprises systemically administering in a pharmaceutically acceptable dosage a compound selected from the group consisting of:
3-(4-acetylaminophenyl)rhodanine;
5-(5-indanylmethylene)rhodanine;
3-(3-acetylphenyl)tetrahydro-2-thioxo-4H-1,3-thiazin-4-one;
3-(2-trifluoromethylphenyl)tetrahydro-2-thioxo-4H-1,3-thiazin-4-one;
3-(3-methylphenyl)tetrahydro-2-thioxo-4H-1,3-thiazin-4-one;
which are non-cytotoxic; and further also selected from the group consisting of:
3-phenylrhodanine;
3-(3-fluorophenyl)-5-acetylaminotetrahydro-2-thioxo-4H-1,3-thiazin-4-one;
3-(3-methoxyphenyl)tetrahydro-2-thioxo-4H-1,3-thiazin-4-one;
3-phenyl-5-carboxymethylene rhodanine;
3-(4-acetyloxyphenyl)tetrahydro-2-thioxo-4H-1,3-thiazin-4-one;
which exhibit a dosage dependent effect in addition to a lack of cytotoxicity.

The novel cyclized ω-carboxyethyl dithiocarbamic acids of this invention according to (a), (b) and (c) are characterized by substituents which include alkylcarbonyl groups and acylamino moieties.

With respect to the alkylcarbonyl substitution referred to above, there are included acetyl; ethylcarbonyl; n-propyl carbonyl; isopropyl carbonyl, n-butylcarbonyl; isobutyl carbonyl, and tertiary-butyl carbonyl moieties.

The acylamino moieties of the above named compounds include acetylamino, n-propionylamino, isopropionylamino, n-butyrylamino, isobutyrylamino, and tertiarybutyrylamino.

Novel compounds of the invention and compounds for methods of producing immunosuppression of the invention are cyclized from ω-carboxyalkyl mono- and di-thiocarbanilic acid intermediates by methods analogous to those known in the art. For example, see the methods referred to in United States Pat. Nos. 3,732,216 and 3,781,434 described above. Both preparation of intermediates and methods used to cyclize the intermediates to obtain cyclized compounds of the present invention are included in the above mentioned U.S. patents as well as in U.S. Pat. No. 4,110,444 and application Ser. No. 848,433, now abandoned.

Accordingly, the intermediates from which the novel cyclized compounds of the present invention are prepared are themselves prepared by reacting the appropriate arylisocyanate or arylisothiocyanate with the appropriate ω-carboxyalkylthiol. The reaction proceeds at ambient temperature, being slightly exothermic, and is ordinarily complete within about one hour. Preferred reaction solvents are benzene, xylene, toluene, aqueous trimethylamine or pyridine.

Recovery of the novel reaction products proceeds by conventional means, e.g., evaporation of solvent, or precipitation with acid. The required starting materials for the transformations to obtain the intermediates are commercially available or can be synthesized by methods well known in the art.

Cyclization of the intermediates to novel compounds of the present invention is accomplished by heating the intermediates on a steam bath with acetic anhydride containing a few drops of concentrated sulfuric acid. Alternative methods of preparation are not excluded herein. Frequently spontaneous cyclization to the 5-membered heterocycles occurs during isolation of the corresponding carboxylic acid.

With respect to the novel method described above for producing immunosuppression in mammals exhibiting hyperimmunity disease, the use of this method in man is especially intended. However, the use in other mammals, such as canine, feline, bovine, and equine species is further intended.

With respect to the transplant rejection phenomenon the present invention relates to allograph rejection phenomena in organ transplantation, particularly vascularized grafts, and including graft-versus host disease in allographic bone marrow transplanatation.

With regard to the autoimmune diseases encompassed by the present method, there is included rheumatoid arthritis, psoriatic arthritis, systemic lupus erythematosus, regional enteritis, chronic active hepatitis, nephrotic syndrome, glomerulonephritis, lupus nephritis, and ulcerative colitis. Further autoimmune diseases included herein are those where a delayed hypersensitivity component has been established such as multiple sclerosis.

In the use of the present invention in transplant rejection phenomena, advantageous results ranging from prolongation of the viability of the transplanted tissue to complete cessation of the rejection process are obtained. In the treatment of autoimmune diseases by the present method, advantageous results ranging from significant symptomatic relief to cessation of the underlying inflammatory process are obtained.

In treatment of the hyperimmunity diseases described above, the requisite clinical end-point is the suppression of the mammal's immune response, thereby effecting amelioration of the hyperimmunity disease. Accordingly, the present invention contemplates use of effective dosages of the compounds of substituted cyclized ω-carboxyalkyl carbanilic, carbamic acids and sulfurized analogs thereof described herein such that the disease progress is first halted and thereafter reversed. Amount of the compounds reqired depends upon a wide variety of factors including the particular compound selected, the age, weight and condition of the mammal being treated, the severity of the particular hyperimmune disease being treated, and the response of the mammal to treatment.

In order to obtain the efficacious results provided by the present invention, any systemic route of administration is acceptable. However, the preferred route of administratiion is by oral method although other systemic routes of adminstration provide equivalent activity at the appropriate dose. Thus, oral, intravenous injection or infusion, subcutaneous injection, or administration in the form of rectal or vaginal suppository represent alternate routes of administration. Regardless of the route of administration selected, the cyclized acids described herein are formulated in a pharmaceutically acceptable form by conventional methods available in the pharmaceutical arts.

Accordingly, when compressed tablets are desired for oral administration a compound of the present invention such as compounds heretofore disclosed is combined with the desired inert ingredients and thereafter compressed by conventional means into a tablet containing the desired quantity of compound. In the case of parenteral administration, sterile solutions for injection of infusion are prepared in accordance with readily available techniques.

After the onset of the hyperimmunity disease has been diagnosed by the attending physician or veterinarian, the treatment with the substituted cyclized mono or dithiocarbanilic acids or the cyclized mono or dithiocarbamic acids in accordance with the present method may be initiated promptly. In cases where the cyclized compounds of the present invention are the sole immunosup-pressive agent to be employed in the treatment of the hyperimmunity disease, an initial dosage between 1.0 and 100 mg./kg./day, preferably 5.0 to 50.0 mg./kg./day, is employed. When initial dosages at the lower end of the above range are employed, the mammals progress is monitored and dosages on subsequent days are increased in the event that the patient or animal response is deemed by the attending physician or veterinarian to be absent or insufficient. When dosages as high as about 100 mg./kg/day are selected, the systemic toxicity of the cyclized compounds must be carefully evaluated and subsequent dosages determined by evaluating the benefits of the drug in relationship to any such toxic manifestations.

For convenience, dosages may be administered once daily or, more preferably, administered at periodic intervals throughout the day. Accordingly, in man the cyclized mono- or dithiocarbanilic acid, and cyclized mono or dithiocarbamic acid derivatives are advantageously administered at 4 or 8 hour intervals throughout the day.

The following examples and preparations describe the manner and process of making and using the invention and set forth the best mode contemplated by the inventor of carrying out the invention but are not to e construed as limiting.

All temperatures are in degrees centigrade.

DESCRIPTION OF THE PREFERRED EMBODIMENTS

Intermediates

Preparation 1:
3-[[[(3-Acetylphenyl)amino]thioxomethyl]thio]-propanoic acid

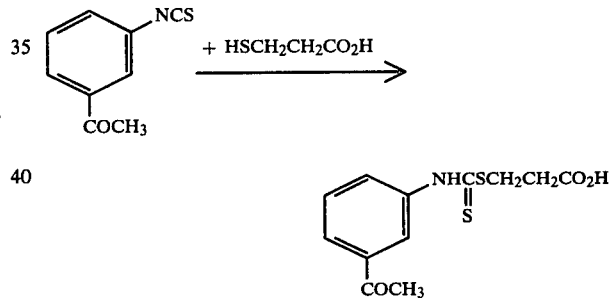

3-Mercaptopropionic acid (5.3 g., 50 mmol) is stirred in 200 ml. pyridine at room temperature. m-Acetyl phenylisothiocyanate (8.9 g., 50.2 mmol) is added and stirred for 30 minutes. Removal of the solvent at 35°/1 mm gives an oil which slowly solidifies. Recrystallization from chloroform-hexane gives a pale yellow solid (5.55 g., 39%) m.p. 143°–145°.

Analysis: Calc'd for $C_{12}H_{13}NO_3S_2$: C. 50.9; H, 4.6; N, 4.9; S, 22.6. Found: C, 51.0; H, 4.6; H, 5.2; S, 22.8.

IR: max (Nujol) 326+ (NH), 1690 (C=O), 1665 (C=O) cm$^{-1}$.

Following the procedure of Preparation 1, but substituting the appropriate substituted phenyl isothiocyanate for m-acetyl phenylisothiocyanate, the appropriate 3-[[[(substituted phenyl)amino]thioxomethyl]thio]propionic acid is prepared as follows:

1. 3-[[[(2-acetylphenyl)amino]thioxomethyl]thio]propionic acid.
2. 3-[[[(4-acetylphenyl)amino]thioxomethyl]thio]propionic acid.
3. 3-[[[(2,3-diacetylphenyl)amino]thioxomethyl]thio]-propanoic acid.

4. 3-[[[(2,4-diacetylphenyl)amino]thioxomethyl]thio]propionic acid.
5. 3-[[[(2,5-diacetylphenyl)amino]thioxomethyl]thio]propionic acid.
6. 3-[[[(2,6-diacetylphenyl)amino]thioxomethyl]thio]propionic acid.
7. 3-[[[(3,4-diacetylphenyl)amino]thioxomethyl]thio]propionic acid.
8. 3-[[[(3,5-diacetylphenyl)amino]thioxomethyl]thio]propionic acid.
9. 3-[[[(2,4,6-triacetylphenyl)amino]thioxomethyl]thio]propionic acid.
10. 3-[[[(2,3,4-triacetylphenyl)amino]thioxomethyl]thio]propionic acid.
11. 3-[[[(3,4,5-triacetylphenyl)amino]thioxomethyl]thio]propionic acid.
12. 3-[[[(2,3,5-triacetylphenyl)amino]thioxomethyl]thio]propionic acid.
13. 3-[[[(2,4,5-triacetylphenyl)amino]thioxomethyl]thio]propionic acid.
14. 3-[[[(2,3,6-triacetylphenyl)amino]thioxomethyl]thio]propionic acid.

Preparation 2:
Bis-3,3'-[sulfonyl-bis(4,1-phenyleneaminocarbonothioylthio)]propionic acid.

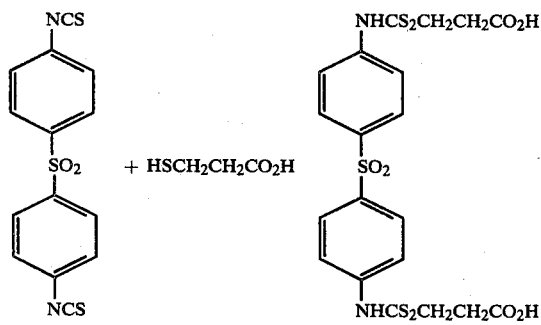

To benzene (100 ml.) is added β-mercaptopropionic acid (3.20 g., 30 mmol), triethylamine (3.10 g., 30 mmol) and bis(4-isothiocyanatophenyl)sulfone (5.0 g., 15 mmol). The mixture is stirred for 30 minutes then 0.1 N NaOH (310 ml., 31 mmol) added. Acidification of the separated aqueous layer with 10% HCl precipitated an off white solid which is recrystallized from methanol-water to leave bis-3,3'-[sulfonyl-bis(4,1-phenyleneaminocarbonothioylthio)]propionic acid as a pale yellow solid (6.08 g.): m.p. 173°-5°.

Analysis: Calc'd for $C_{20}H_{20}N_{20}N_2O_6S_5$: C, 44.1; H, 3.7; N, 5.1; S, 29.4. Found: C, 44.0; H, 3.7; N, 5.1; S, 28.0.

IR: max (Nujol) 3200 (NH) 1700 (C=O) cm$^{-1}$.

Following the procedure of Preparation 2, but substituting an appropriate bis(isothiocyanatophenyl)sulfone the corresponding bis-3 compound is prepared as follows:

1. bis-3,3'-[sulfonyl-bis(3,1-phenyleneaminocarbonothioylthio)]propionic acid.
2. bis-3,3'-[sulfonyl-bis(2,1-phenyleneaminocarbonothioylthio)]propionic acid.

Preparation 3:
3-[[[(pentafluorophenyl)amino]thioxomethyl]thio]propanoic acid.

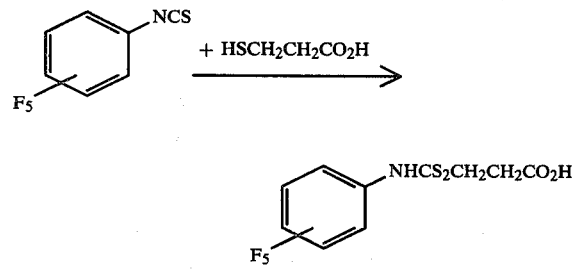

Pentafluorophenylisothiocyanate (2.25 g., 10 mmol) and β-mercaptopropionic acid (1.1 g., 10 mmol) are stirred at room temperature in 25% aqueous trimethylamine (15 ml.). The flask is cooled in ice and acidified with conc. HCl. A yellow gummy material separated, which is filtered, washed with water then dissolved in ether (100 ml.) and dried over MgSO$_4$. Removal of the solvent gives a pale yellow viscous oil (3.4 g.), which slowly crystallizes. Several attempts at recystallizations do not give homogenous material. Chromatography over SiO$_2$ with 1:99 acetic acid:chloroform as eluent give pure material which is recrystallized from ether-hexane as white plates of 3-[[[(pentafluorophenyl)amino]thioxomethyl]thio]propanoic acid m.p. 126.5°-129.0°.

Analysis: Calc'd for $C_{10}H_6F_5NO_2S_2$: C, 36.3; H, 1.8; N, 4.2; S, 19.3; F, 28.7. Found: C, 36.4; H, 1.8; N, 4.7; S, 19.2; F, 28.6.

IR: max (Nujol) 3175 (NH), 1704 (C=O) cm$^{-1}$.

Following the procedure of Preparation 3 but substituting the appropriate tri or tetra fluorophenylisothiocyanate the corresponding propionic acid is formed as follows:

3-[[[(2,3,4-trifluorophenyl)amino]thioxomethyl]thio]propionic acid,
3-[[[(3,4,5-trifluorophenyl)amino]thioxomethyl]thio]propionic acid,
3-[[[(2,4,6-trifluorophenyl)amino]thioxomethyl]thio]propionic acid,
3-[[[(2,3,5-trifluorophenyl)amino]thioxomethyl]thio]propionic acid,
3-[[[(2,4,5-trifluorophenyl)amino]thioxomethyl]thio]propionic acid,
3-[[[(2,5,6-trifluorophenyl)amino]thioxomethyl]thio]propionic acid,
3-[[[(2,3,4,5-tetrafluorophenyl)amino]thioxomethyl]thio]propionic acid,
3-[[[(2,4,5,6-tetrafluorophenyl)amino]thioxomethyl]thio]propionic acid,
3-[[[(2,3,5,6-tetrafluorophenyl)amino]thioxomethyl]thio]propionic acid.

EXAMPLE 1

3-(3-Acetylphenyl)tetrahydro-2-thioxo-4H-1,3-thiazin-4-one.

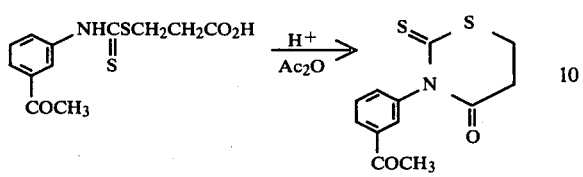

The propanoic acid (3.0 g., 10.6 mmol) is heated on a steam bath for 10 minutes in acetic anhydride (15 ml.) containing 3 drops conc. $H_2SO_4$. Upon cooling the solid is filtered (2.6 g., 93%) and recrystallized from chloroform-hexane to afford a yellow solid (1.6 g., 57%) m.p. 197°–199°.

Analysis: Calc'd for $C_{12}H_{11}NO_2S_2$: C, 54.3; H, 4.2; N, 5.3; S, 24.2. Found: C, 52.9; H, 4.4; N, 5.3; S, 23.8.

IR: max (Nujol) 1702 (C=O), 1674 (C=O) cm$^{-1}$.

Following the procedure of Example 1, but using the corresponding 3-[[[(mono, di and tri substituted acetylphenyl)amino]thioxomethyl]thio]propionic acid, there is obtained a corresponding product:

1. 3-(2-Acetylphenyl)tetrahydro-2-thioxo-4H-1,3-thiazin-4-one.
2. 3-(4-Acetylphenyl)tetrahydro-2-thioxo-4H-1,3-thiazin-4-one.
3. 3-(2,3-Diacetylphenyl)tetrahydro-2-thioxo-4H-1,3-thiazin-4-one.
4. 3-(2,4-Diacetylphenyl)tetrahydro-2-thioxo-4H-1,3-thiazin-4-one.
5. 3-(2,5-Diacetylphenyl)tetrahydro-2-thioxo-4H-1,3-thiazin-4-one.
6. 3-(2,6-Diacetylphenyl)tetrahydro-2-thioxo-4H-1,3-thiazin-4-one.
7. 3l-(3,4-Diacetylphenyl)tetrahydro-2-thioxo-4H-1,3-thiazin-4-one.
8. 3-(3,5-Diacetylphenyl)tetrahydro-2-thioxo-4H-1,3-thiazin-4-one.
9. 3-(2,4,6-Triacetylphenyl)tetrahydro-2-thioxo-4H-1,3-thiazin-4-one.
10. 3-(2,3,4-Triacetylphenyl)tetrahydro-2-thioxo-4H-1,3-thiazin-4-one.
11. 3-(3,4,5-Triacetylphenyl)tetrahydro-2-thioxo-4H-1,3-thiazin-4-one.
12. 3-(2,3,5-Triacetylphenyl)tetrahydro-2-thioxo-4H-1,3-thiazin-4-one.
13. 3-(2,3,6-Triacetylphenyl)tetrahydro-2-thioxo-4H-1,3-thiazin-4-one.
14. 3-(2,4,5-Triacetylphenyl)tetrahydro-2-thioxo-4H-1,3-thiazin-4-one.

EXAMPLE 2

Bis-4,4-(3,3'-tetrahydro-2-thioxo-1,3-thiazinyl-4-one)-diphenylsulfone.

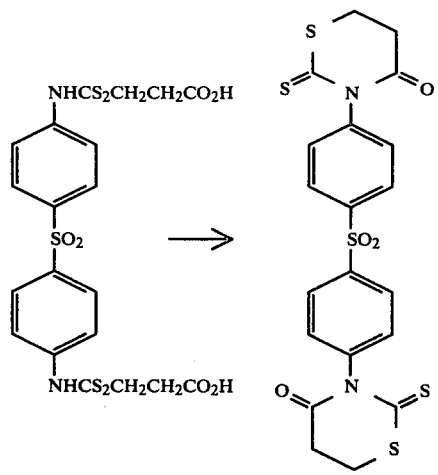

To the dithiocarbamate of Preparation 2 (3.0 g., 5.5 mmol), in acetic anhydride (15 ml.) is added 1 drop of conc. $H_2SO_4$, and the reaction heated on a steam bath for 30 minutes. On cooling a solid crystallized (2.75 g.) which is recrystallized from dimethylformamide-water to yield bis-4,4'-(3,3'-tetrahydro-2-thioxo-1,3-thiazinyl-4-one)diphenylsulfone as yellow crystals (1.80 g.), m.p. 292°–294°.

Analysis: Calc'd for $C_{20}H_{16}N_2O_4S_5$: C, 47.2; H, 3.2; N, 5.5; S, 31.5. Found: C, 47.3; H, 3.5; N, 5.7; S, 30.9.

IR: max (Nujol) 1705 (C=O) cm$^{-1}$.

Following the procedure of Example 2, but using an appropriate intermediate, bis-3,3'[sulfonyl-bis-(phenyleneaminocarbonothioxo)]propionic acid, there is obtained a corresponding product as follows:

1. Bis-3,3'-(3,3'-tetrahydro-2-thioxo-1,3-thiazinyl-4-one)diphenylsulfone.
2. Bis-2,2'-(3,3'-tetrahydro-2-thioxo-1,3-thiazinyl-4-one)diphenylsulfone.

EXAMPLE 3

3-(Pentafluorophenyl)tetrahydro-2-thioxo-4H-1,3-thiazin-4-one.

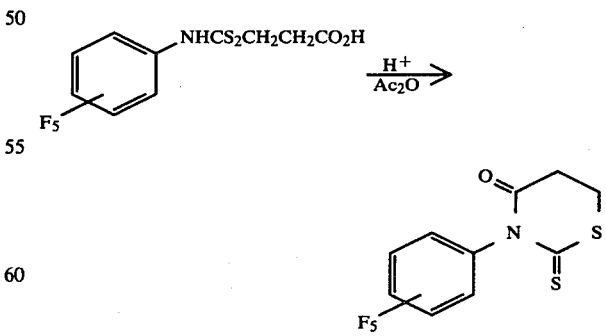

The carboxylic acid, 3-[[[(pentafluorophenyl)amino]-thioxomethyl]thio]propionic acid (500 mg., 1.51 mmol) is dissolved in acetic anhydride (5 ml.) to give a bright yellow solution. A drop of conc. $H_2SO_4$ is added and the solution heated on a steam bath for 2–3 minutes. On cooling, crystals separated, which are recrystallized from ethanol to give pure 3-(pentafluorophenyl)tetrahydro-2-thioxo-4H-1,3-thiazin-4-one as bright yellow translucent crystals (320 mg.) m.p. 163.5°–164.5°.

Analysis: Calc'd. for $C_{10}H_4F_5NOS_2$: C, 38.3; H, 1.3; N, 4.5; S, 20.4; F, 30.3. Found: C, 38.5; H, 1.1; N, 4.6; S, 20.4; F, 29.9.

IR: max (Nujol) 1730 (C=O) cm$^{-1}$.

Following the procedure of Example 3 but using an appropriate tri or tetra fluorophenyl amino[[thioxomethyl]thio]propionic acid there is obtained a corresponding product as follows:

1. 3-(3,4,5-trifluorophenyl)tetrahydro-2-thioxo-4H-1,3-thiazin-4-one.
2. 3-(2,3,4-trifluorophenyl)tetrahydro-2-thioxo-4H-1,3-thiazin-4-one.
3. 3-(2,4,6-trifluorophenyl)tetrahydro-2-thioxo-4H-1,3-thiazin-4-one.
4. 3-(2,3,5-trifluorophenyl)tetrahydro-2-thioxo-4H-1,3-thiazin-4-one.
5. 3-(2,4,5-trifluorophenyl)tetrahydro-2-thioxo-4H-1,3-thiazin-4-one.
6. 3-(2,5,6-trifluorophenyl)tetrahydro-2-thioxo-4H-1,3-thiazin-4-one.
7. 3-(2,3,4,5-tetrafluorophenyl)tetrahydro-2-thioxo-4H-1,3-thiazin-4-one.
8. 3-(2,4,5,6-tetrafluorophenyl)tetrahydro-2-thioxo-4H-1,3-thiazin-4-one.
9. 3-(2,3,5,6-tetrafluorophenyl)tetrahydro-2-thioxo-4H-1,3-thiazin-4-one.

EXAMPLE 4

3-(3-Fluorophenyl)tetrahydro-2-thioxo-5-acetylamino-4H-1,3-thiazin-4-one.

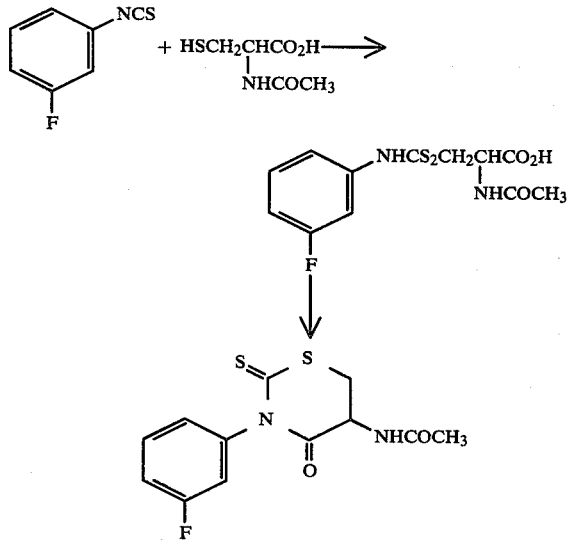

N-Acetylcysteine (2.36 g., 20 mmol) is mixed with benzene (50 ml.) and triethylamine (2.02 g., 20 mmol) followed by 3-fluorophenylisothiocyanate (3.06 g., 20 mmol). The reaction is stirred for 15 minutes when 0.1 N-NaOH solution (200 ml., 20 mmol) is added followed by ether (50 ml.). The aqueous layer is separated and acidified with 10% HCl. A yellow oil separated which is extracted with ethylacetate (200 ml.) and dried over MgSO$_4$. Filtration and removal of the solvent gives a yellow foam (4.7 g.). Chromatography over SiO$_2$ eluting with acetic acid-chloroform mixtures produces a yellow gum (4.3 g.) of the intermediate dithiocarbamate. The gum is partitioned between ether (250 ml.) and water (150 ml.); the ether is washed with 2×150 ml. water. After drying (MgSO$_4$), the ether layer affords a yellow foam (3.0 g.). The aqueous layers affords a similar yellow foam (870 mg.) upon evaporation, identical in all respects to the former yellow foam. The latter material (870 mg.) is treated with acetic anhydride (5 ml.) and 3 crops conc. H$_2$SO$_4$ to give a brilliant yellow solution. The solution is heated for 5 minutes on a steam bath, cooled and water (150 ml.) added to give a yellow gum. Extraction with 2×150 ml. ethylacetate gives a yellow glass (800 mg.). Chromatography over SiO$_2$, eluting with 1:9 methanol:chloroform gives a yellow solid (650 mg.). Several recrystallizations gives small yellow granules of 3-(3-fluorophenyl)tetrahydro-2-thioxo-5-acetylamino-4H-1,3-thiazin-4-one, m.p. 176°–7°.

Analysis: Calc'd for $C_{12}H_{11}FN_2O_2S_2$: C, 48.3; H, 3.7; H, 9.4. Found: C, 48.5; H, 3.7; N, 9.5.

IR: max (Nujol) 3330 (NH), 1720 (C=O), 1670 (C=O) cm$^{-1}$.

Following the procedures of Example 4 but using an appropriate intermediate selected from a [[[(mono, di, tri, tetra and penta fluoro substituted phenyl)[thioxomethyl]thio]propionic acid there is a corresponding product:

1. 3-(2-fluorophenyl)tetrahydro-2-thioxo-5-acetylamino-4H-1,3-thiazin-4-one.
2. 3-(4-fluorophenyl)tetrahydro-2-thioxo-5-acetylamino-4H-1,3-thiazin-4-one.
3. 3-(2,3-difluorophenyl)tetrahydro-2-thioxo-5-acetylamino-4H-1,3-thiazin-4-one.
4. 3-(2,4-difluorophenyl)tetrahydro-2-thioxo-5-acetylamino-4H-1,3-thiazin-4-one.
5. 3-(2,5-difluorophenyl)tetrahydro-2-thioxo-5-acetylamino-4H-1,3-thiazin-4-one.
6. 3-(2,6-difluorophenyl)tetrahydro-2-thioxo-5-acetylamino-4H-1,3-thiazin-4-one.
7. 3-(3,4-difluorophenyl)tetrahydro-2-thioxo-5-acetylamino-4H-1,3-thiazin-4-one.
8. 3-(3,5-difluorophenyl)tetrahydro-2-thioxo-5-acetylamino-4H-1,3-thiazin-4-one.
9. 3-(2,4,6-trifluorophenyl)tetrahydro-2-thioxo-5-acetylamino-4H-1,3-thiazin-4-one.
10. 3-(2,3,4-trifluorophenyl)tetrahydro-2-thioxo-5-acetylamino-4H-1,3-thiazin-4-one.
11. 3-(3,4,5-trifluorophenyl)tetrahydro-2-thioxo-5-acetylamino-4H-1,3-thiazin-4-one.
12. 3-(2,3,5-trifluorophenyl)tetrahydro-2-thioxo-5-acetylamino-4H-1,3-thiazin-4-one.
13. 3-(2,4,5-trifluorophenyl)tetrahydro-2-thioxo-5-acetylamino-4H-1,3-thiazin-4-one.
14. 3-(2,3,6-trifluorophenyl)tetrahydro-2-thioxo-5-acetylamino-4H-1,3-thiazin-4-one.
15. 3-(2,3,4,5-tetrafluorophenyl)tetrahydro-2-thioxo-5-acetylamino-4H-1,3-thiazin-4-one.
16. 3-(2,3,5,6-tetrafluorophenyl)tetrahydro-2-thioxo-5-acetylamino-4H-1,3-thiazin-4-one.
17. 3-(2,3,4,6-tetrafluorophenyl)tetrahydro-2-thioxo-5-acetylamino-4H-1,3-thiazin-4-one.
18. 3-(2,3,4,5,6-pentafluorophenyl)tetrahydro-2-thioxo-5-acetylamino-4H-1,3-thiazin-4-one.

Following the procedures of Preparations 1, 2, and 3 the intermediates of the following Tables I, II, and III, respectively are prepared from corresponding reactants:

TABLE I

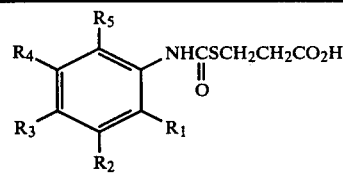

| R1 | R2 | R3 | R4 | R5 |
|---|---|---|---|---|
| COCH3 | H | H | H | H |
| H | COCH3 | H | H | H |
| H | H | COCH3 | H | H |
| H | COCH3 | H | H | COCH3 |
| COCH3 | H | H | H | COCH3 |
| COCH3 | COCH3 | H | H | H |
| COCH3 | H | COCH3 | H | H |
| H | COCH3 | H | COCH3 | H |
| H | H | COCH3 | COCH3 | H |
| COCH3 | COCH3 | COCH3 | H | H |
| COCH3 | H | COCH3 | H | COCH3 |
| H | —COCH3 | —COCH3 | —COCH3 | H |
| —COCH3 | —COCH3 | H | —COCH3 | H |
| —COCH3 | H | H | —COCH3 | —COCH3 |
| H | —COCH3 | —COCH3 | H | —COCH3 |
| H | H | -S(=O)2-C6H4-NHC(=O)SCH2CH2C(=O)OH (para) | H | H |
| H | H | -C6H4(3-SO2CH3)-NHC(=O)SCH2CH2C(=O)OH | H | H |
| -C6H4(2-SO2)-NHC(=O)SCH2CH2C(=O)OH | H | H | H | H |
| F | F | F | F | F |
| F | H | F | H | F |
| F | F | F | H | H |
| H | F | F | F | H |
| F | F | H | F | H |
| F | H | H | F | F |
| F | F | F | H | H |
| F | H | F | F | F |
| F | F | H | F | F |

Following the procedures of Examples 1, 2, and 3, novel compounds of the following Table II are prepared from the corresponding intermediates of Table I.

TABLE II

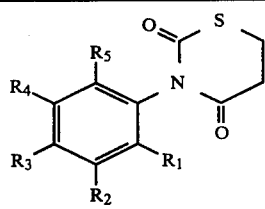

| R1 | R2 | R3 | R4 | R5 |
|---|---|---|---|---|
| COCH3 | H | H | H | H |
| H | COCH3 | H | H | H |
| H | H | COCH3 | H | H |

TABLE II-continued

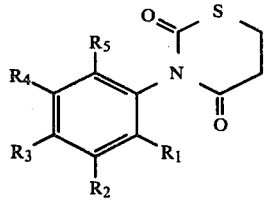

| R₁ | R₂ | R₃ | R₄ | R₅ |
|---|---|---|---|---|
| COCH₃ | H | H | COCH₃ | H |
| COCH₃ | H | H | H | COCH₃ |
| COCH₃ | COCH₃ | H | H | H |
| COCH₃ | H | COCH₃ | H | H |
| H | COCH₃ | H | COCH₃ | H |
| H | COCH₃ | COCH₃ | H | H |
| COCH₃ | COCH₃ | COCH₃ | H | H |
| COCH₃ | H | COCH₃ | H | COCH₃ |
| H | —COCH₃ | —COCH₃ | —COCH₃ | H |
| —COCH₃ | —COCH₃ | H | —COCH₃ | H |
| —COCH₃ | H | H | —COCH₃ | —COCH₃ |
| COCH₃ | H | —COCH₃ | —COCH₃ | H |
| H | H | 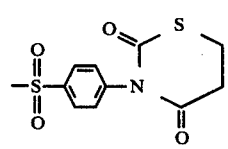 | H | H |
| H | 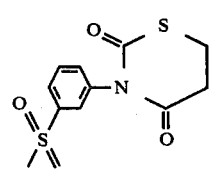 | H | H | H |
| 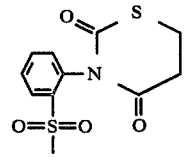 | H | H | H | H |
| F | F | F | F | F |
| F | H | F | H | F |
| F | F | F | H | H |
| H | F | F | F | H |
| F | F | H | F | H |
| F | H | F | F | H |
| F | F | H | F | F |
| F | F | H | F | H |
| F | H | F | F | F |
| F | F | H | F | F |

Following the procedures of Example 4, novel compounds of the following Table III are prepared from corresponding reactants, themselves known in the art.

TABLE III

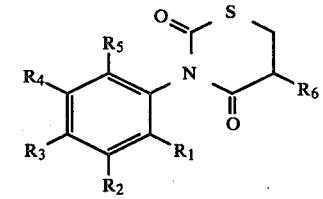

| R₁ | R₂ | R₃ | R₄ | R₅ | R₆ |
|---|---|---|---|---|---|
| F | F | F | F | F |  CH₃CNH— |

TABLE III-continued

![structure](R1-R6 phenyl thiazine structure)

| R1 | R2 | R3 | R4 | R5 | R6 |
|---|---|---|---|---|---|
| F | H | H | H | H | CH₃C(O)NH— |
| H | F | H | H | H | CH₃C(O)NH— |
| H | H | F | H | H | CH₃C(O)NH— |
| F | F | H | H | H | CH₃C(O)NH— |
| F | H | F | H | H | CH₃C(O)NH— |
| F | H | H | F | H | CH₃C(O)NH— |
| F | H | H | H | F | CH₃C(O)NH— |
| H | F | F | H | H | CH₃C(O)NH— |
| H | F | H | F | H | CH₃C(O)NH— |
| H | F | F | H | F | CH₃C(O)NH— |
| F | H | F | H | F | CH₃C(O)NH— |
| F | F | F | H | H | CH₃C(O)NH— |
| H | F | F | F | H | CH₃C(O)NH— |
| F | F | H | F | H | CH₃C(O)NH— |
| F | F | H | H | F | CH₃C(O)NH— |
| F | F | F | F | H | CH₃C(O)NH— |
| F | F | H | F | F | CH₃C(O)NH— |

TABLE III-continued

| R1 | R2 | R3 | R4 | R5 | R6 |
|---|---|---|---|---|---|
| F | F | F | H | F | CH₃C(O)NH— |

We claim:

1. A compound selected from the group consisting of:

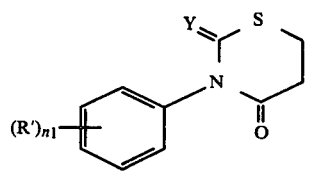 (a)

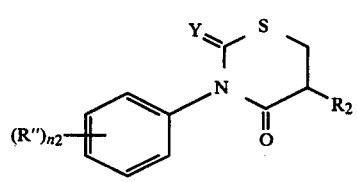 (b)

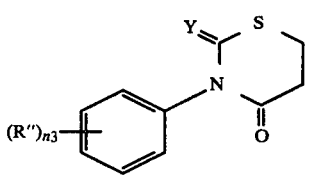 (c)

wherein R' is alkylcarbonyl with the alkyl of from one to four carbon atoms, inclusive, or

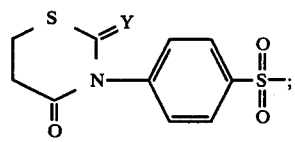

R" is selected from the group consisting of chlorine, fluorine, bromine and trifluoromethyl; $R_2$ is selected from the group consisting of acylamino with acyl of from one to four carbon atoms, inclusive; $n_1$ is an integer of from one to three; $n_2$ is an integer of from one to five; $n_3$ is an integer of from three to five; Y is selected from the group consisting of sulfur and oxygen.

2. A compound according to claim 1 wherein Y is sulfur.

3. A compound according to claim 2 having the formula:

4. A compound according to claim 2 having the formula:

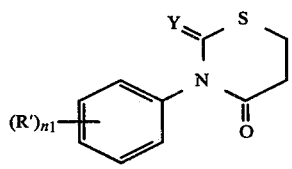

5. A compound according to claim 2 having the formula:

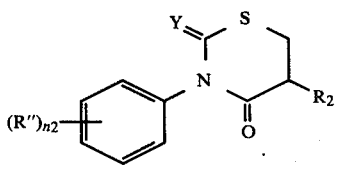

6. 3-(Acetylphenyl)tetrahydro-2-thioxo-4H-1,3-thiazin-4-one, a compound according to claim 5.

7. Bis-4,4'-(3,3'-tetrahydro-2-thioxo-4H-1,3-thiazinyl-4-one)diphenylsulfone, a compound according to claim 5.

8. 3-(3-Fluorophenyl)-5-acetylaminotetrahydro-2-thioxo-4H-1,3-thiazin-4-one, a compound according to claim 5.

9. A compound according to claim 5 wherein $n_3$ is the integer four or five.

10. 3-(Pentafluorophenyl)tetrahydro-2-thioxo-4H-1,3-thiazin-4-one, a compound according to claim 9.

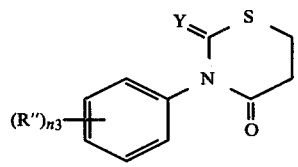

UNITED STATES PATENT OFFICE
CERTIFICATE OF CORRECTION

Patent No. 4,352,929                Dated   October 5, 1982

Inventor(s) David J. Anderson and Barbara E. Loughman

It is certified that error appears in the above-identified patent and that said Letters Patent are hereby corrected as shown below:

Column 1, line 35, "a is" should read -- wherein a is --.
Column 1, line 50, "2. The" should read -- The --.
Column 2, line 54, "lymphold" should read -- lymphoid --.
Column 4, line 52, "$n_2$" should read -- wherein $n_2$ --.
Column 5, line 50, "$n_2$" should read -- wherein $n_2$ --.
Column 7, line 3, "transplanatation" should read -- transplantation --.
Column 7, line 30, "reqired" should read -- required --.
Column 7, line 39, "administratiion" should read -- administration --.
Column 7, line 40, "adminstration" should read -- administration --.
Column 8, line 21, "to e" should read -- to be --.
Column 9, line 55, "$C_{20}N_{20}N_{20}N_2O_6S_5$" should read -- $N_{20}H_{20}N_2O_6S_5$ --.
Column 11, line 48, "7. 31-(3,4-" should read -- 7. 3-(3,4- --.
Column 12, line 34, "$C_{20}h_{16}N_2O_4S_5$:" should read -- $C_{20}H_{16}N_2O_4S_5$; --.

Signed and Sealed this

Sixteenth Day of October 1984

[SEAL]

Attest:

GERALD J. MOSSINGHOFF

Attesting Officer

Commissioner of Patents and Trademarks